(12) United States Patent
Nakamura

(10) Patent No.: US 7,658,112 B2
(45) Date of Patent: Feb. 9, 2010

(54) MAT FOR PRESSURE MEASUREMENT AND A BODY INFORMATION ACQUISITION DEVICE

(75) Inventor: Yuji Nakamura, Tokyo (JP)

(73) Assignee: Tanita Corporation, Tokyo (JP)

( * ) Notice: Subject to any disclaimer, the term of this patent is extended or adjusted under 35 U.S.C. 154(b) by 16 days.

(21) Appl. No.: 12/038,324

(22) Filed: Feb. 27, 2008

(65) Prior Publication Data

US 2009/0056465 A1 Mar. 5, 2009

(30) Foreign Application Priority Data

Feb. 28, 2007 (JP) ............................. 2007-048253

(51) Int. Cl.
*G01L 7/10* (2006.01)
(52) U.S. Cl. ..................................................... 73/731
(58) Field of Classification Search .................. 73/731; 5/713, 710
See application file for complete search history.

(56) References Cited

U.S. PATENT DOCUMENTS

| | | | | |
|---|---|---|---|---|
| 4,949,413 | A | * | 8/1990 | Goodwin ........................ 5/713 |
| 5,184,112 | A | | 2/1993 | Gusakov et al. |
| 5,873,137 | A | * | 2/1999 | Yavets-Chen ................... 5/713 |
| 6,273,810 | B1 | * | 8/2001 | Rhodes et al. ............... 454/120 |
| 2006/0169282 | A1 | | 8/2006 | Izumi et al. |
| 2007/0107133 | A1 | * | 5/2007 | Schwaiger et al. ............. 5/713 |
| 2007/0204698 | A1 | * | 9/2007 | Fukutomi et al. ............. 73/728 |

FOREIGN PATENT DOCUMENTS

| | | |
|---|---|---|
| JP | 2000-000215 | 1/2000 |
| JP | 2006-280686 | 10/2006 |
| WO | WO 91/13575 | 9/1991 |
| WO | WO 2004/073577 | 9/2004 |
| WO | WO 2005/082252 | 9/2005 |

* cited by examiner

*Primary Examiner*—Andre J Allen
(74) *Attorney, Agent, or Firm*—Paul F. Neils, Esq.; Ackerman Senterfitt

(57) ABSTRACT

When the distribution of the pressure applied to a mat is measured, a plurality of detection units is established in the air mat and the sensor for measuring the pressure applied to the air mat is needed to be provided for each detection unit. The mat for pressure measurement 2 is arranged the first medium accommodation object 21*b* on the right side and the second medium accommodation object 22*b* on the left side. The first connecting pipeline 21*a* is connected to the first medium accommodation object 21*b* and the second connecting pipeline 22*a* is connected to the second medium accommodation object 22*b*, respectively. Since the internal diameter K4 of the second connecting 22*a* is set smaller than the internal diameter K2 of the first connecting pipeline 21*a* and the pipeline length of the second connecting pipeline 22*a* is set longer than that of the first connecting pipeline 21*a* in the mat for pressure measurement 2, the pressure loss coefficient of the second connecting pipeline 22*a* has a greater value than that of the first connecting pipeline 21*a*.

5 Claims, 11 Drawing Sheets

[Fig.1]
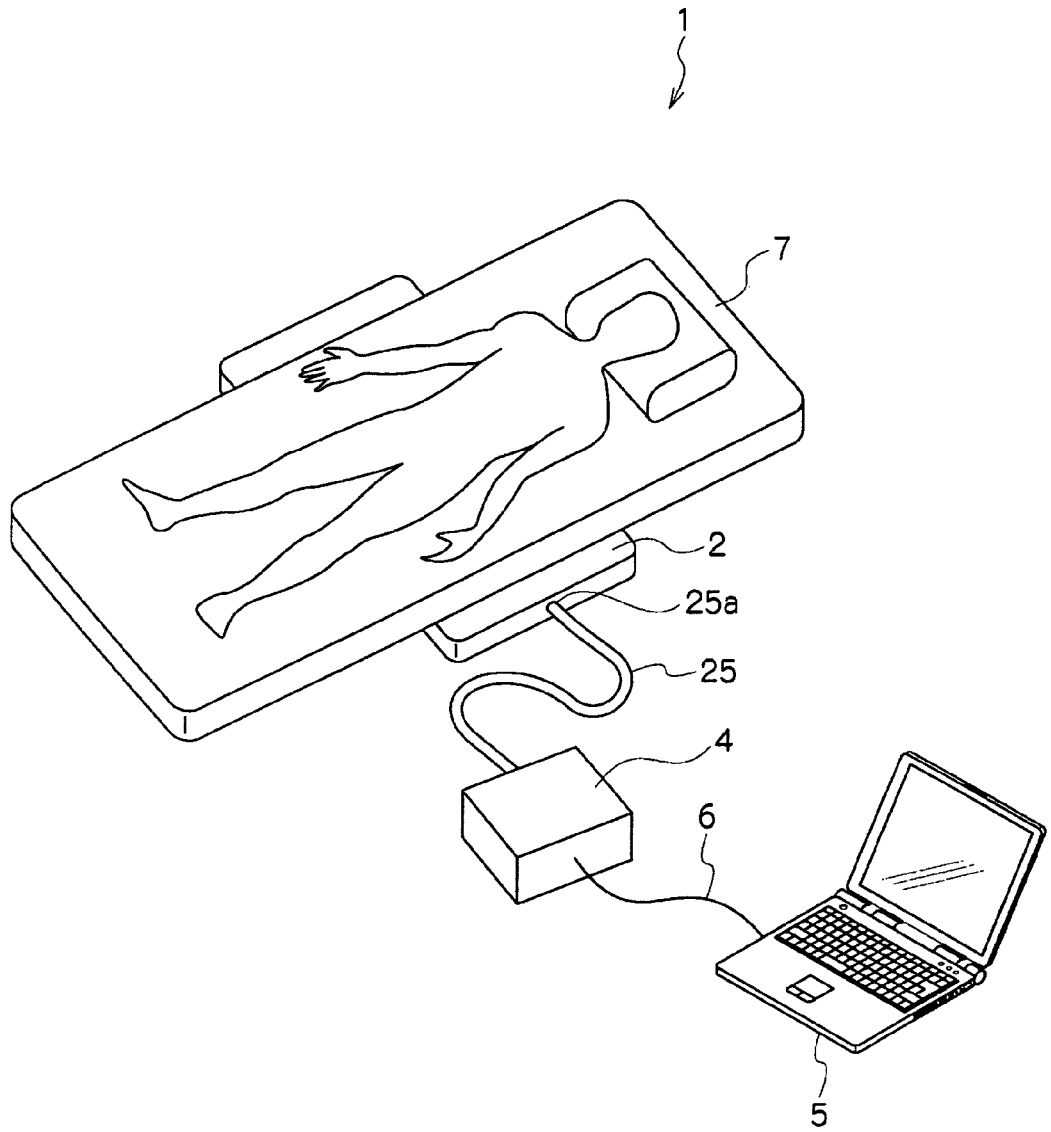

[Fig.2]
(a)
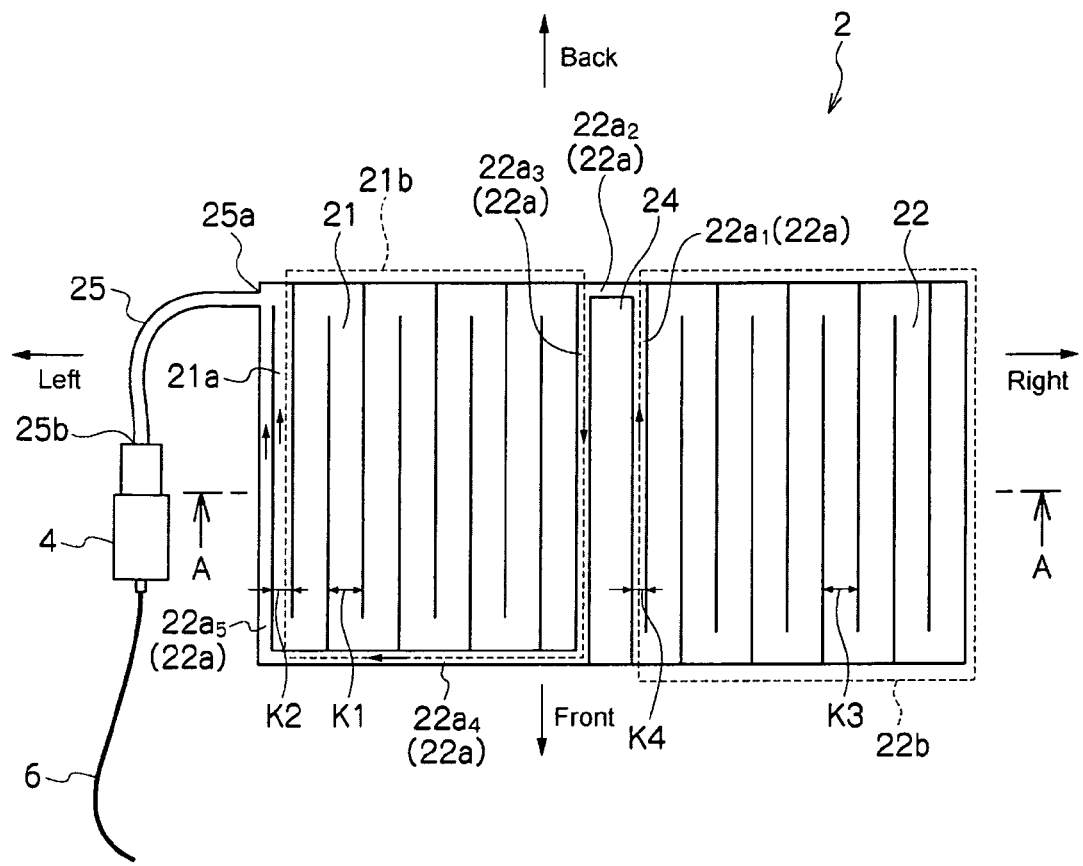
(b)
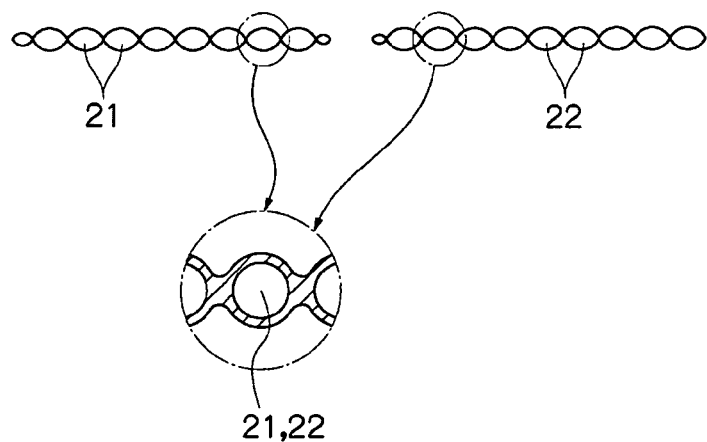

[Fig.3]
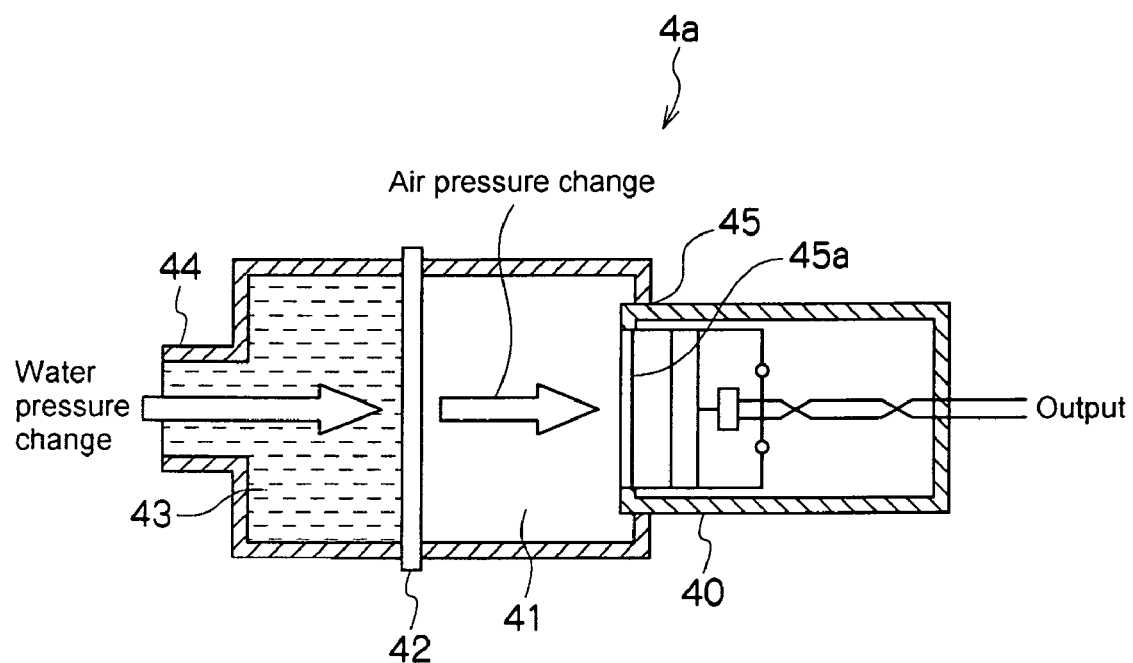

[Fig.4]
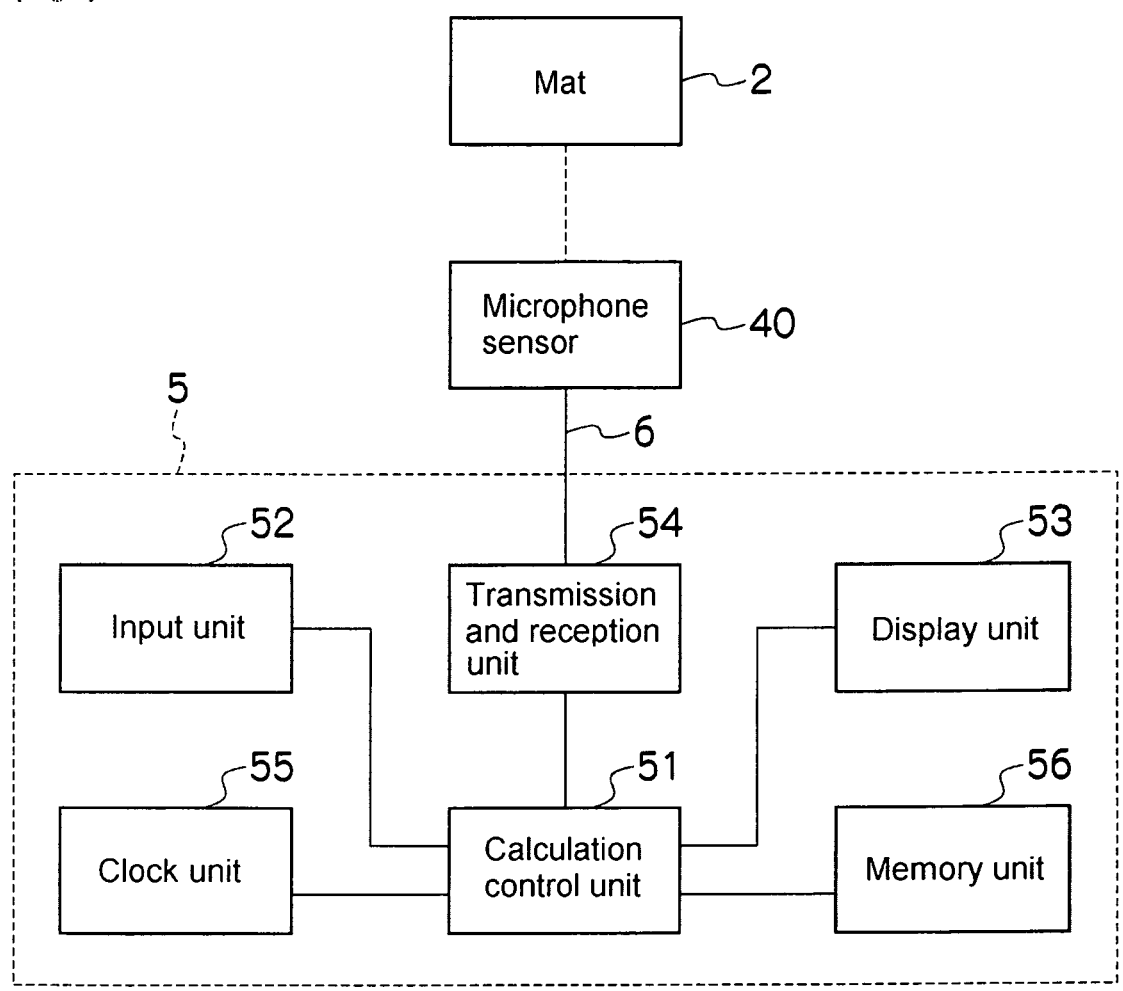

[Fig.9]
(a)
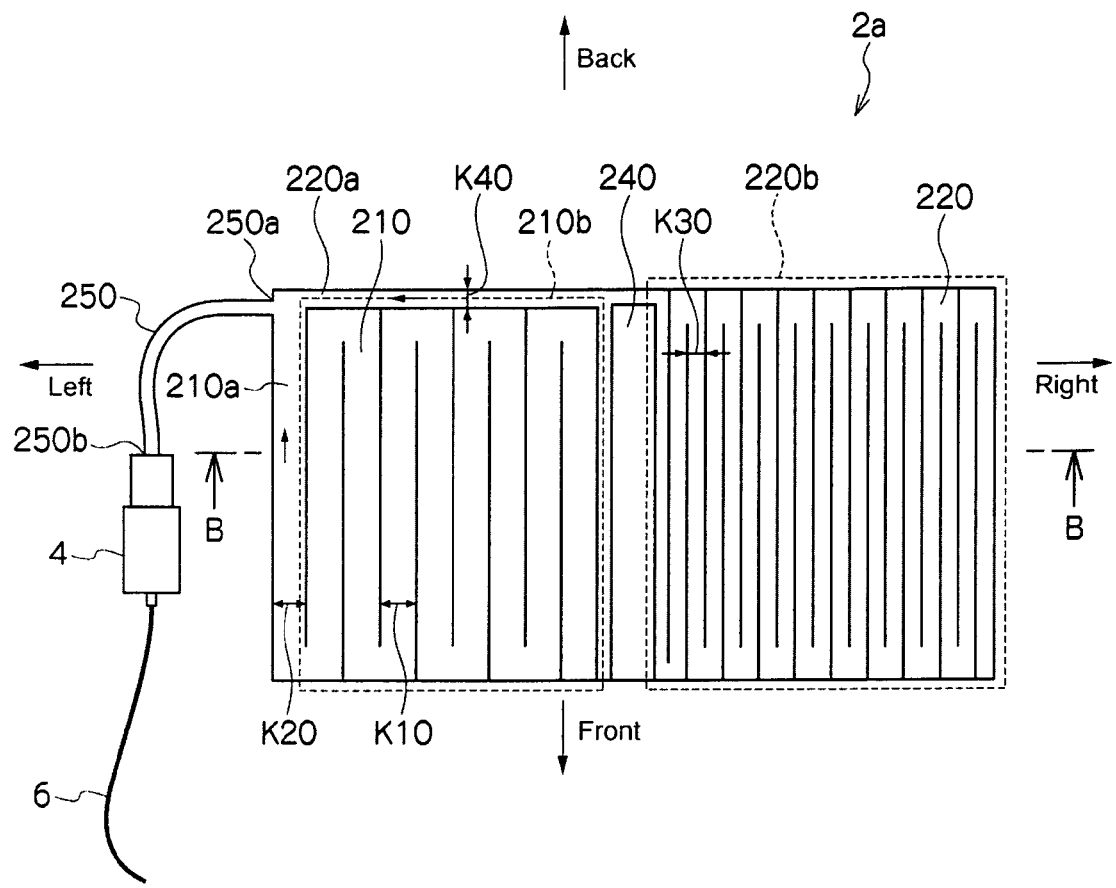
(b)
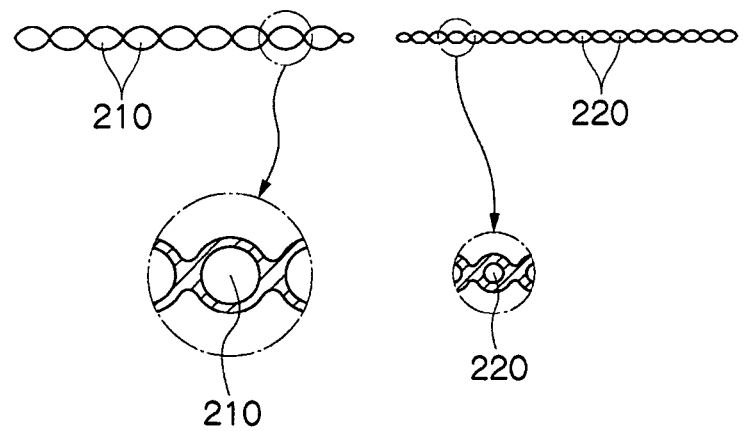

[Fig.10]
(a)
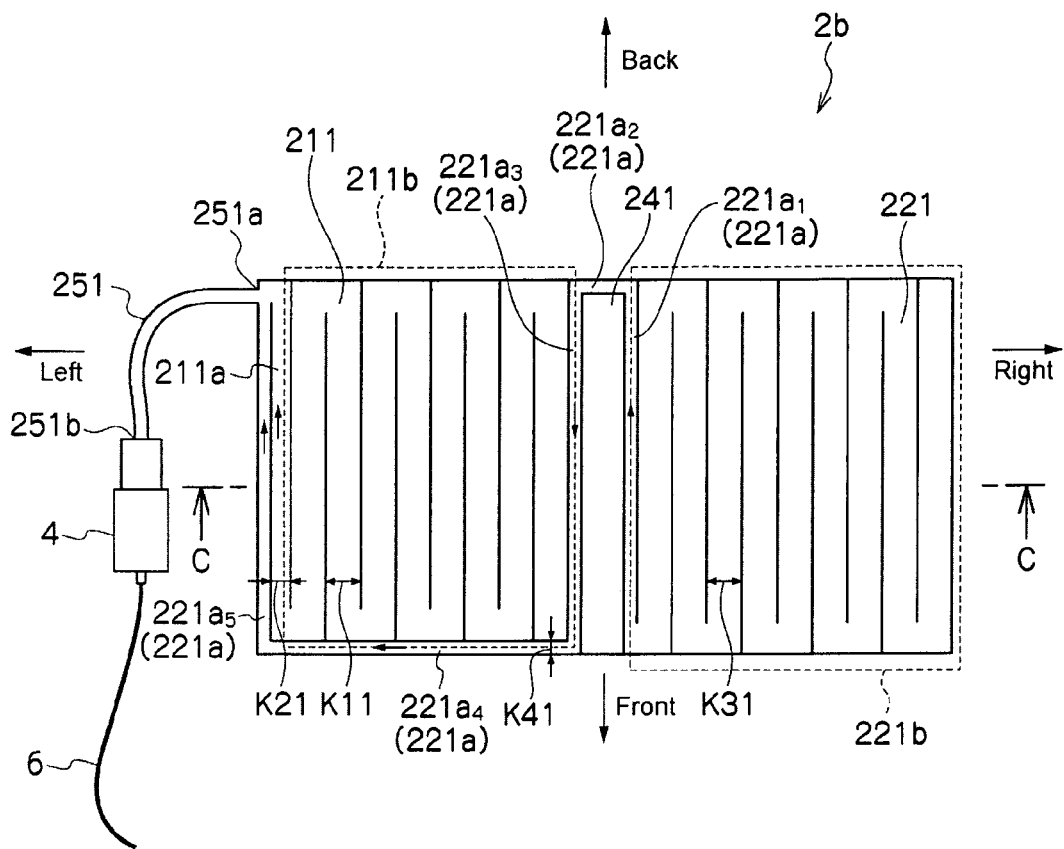
(b)
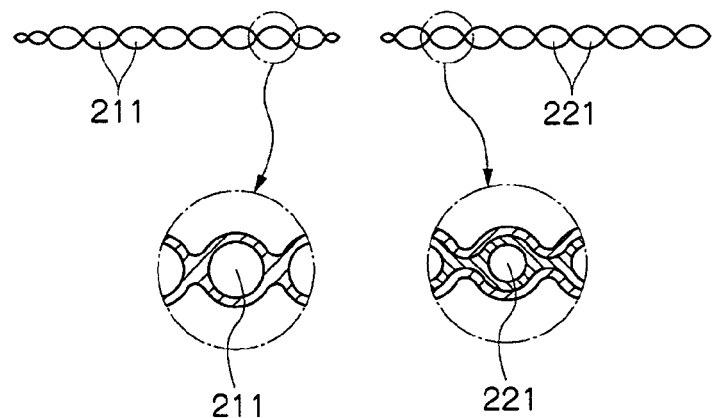

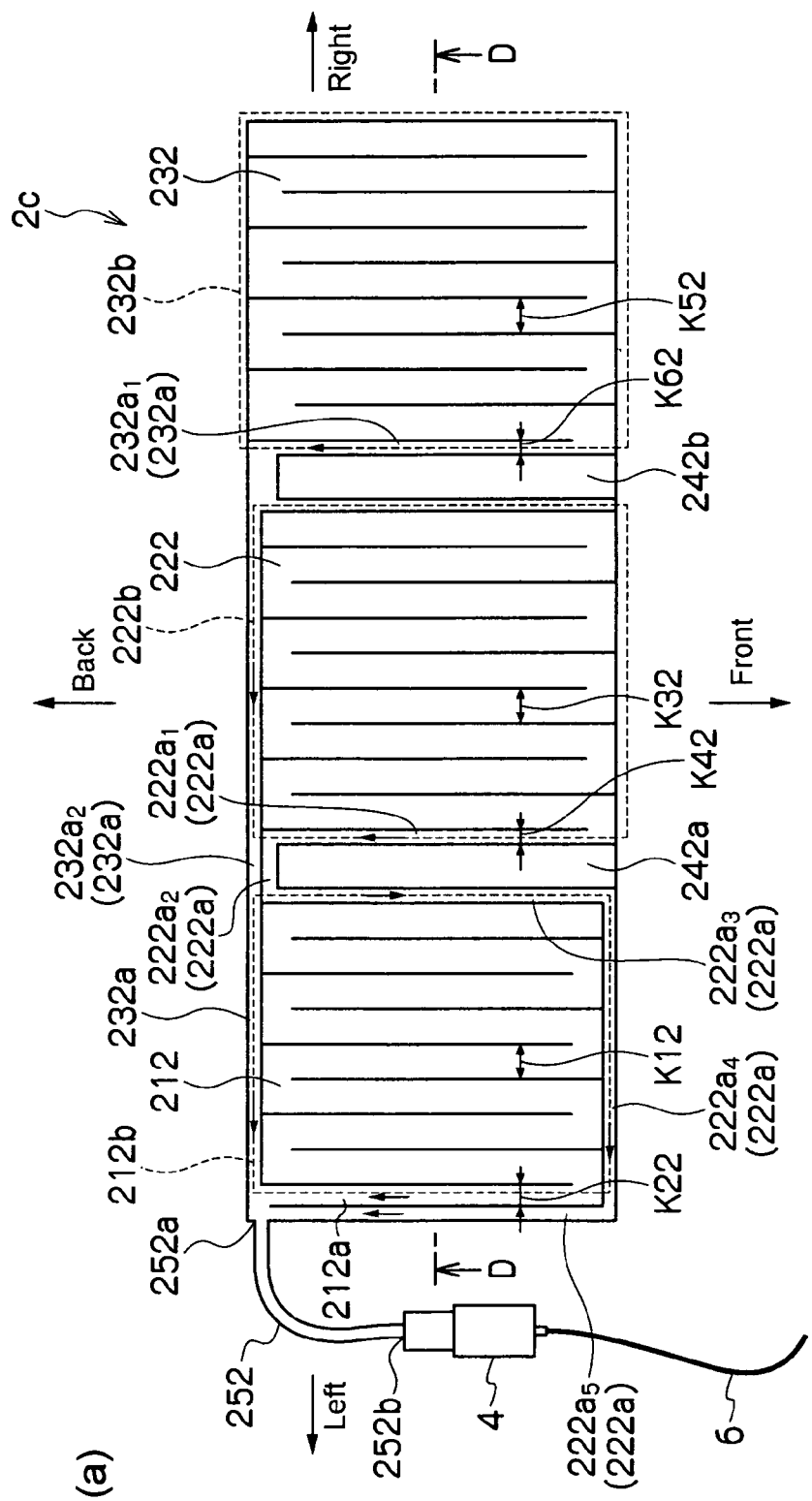
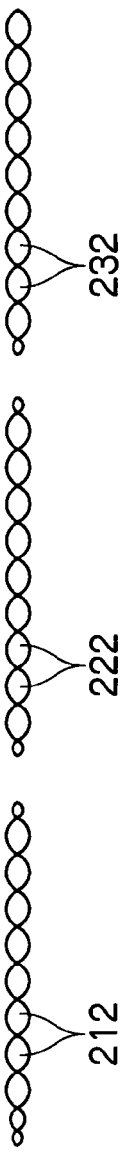
FIG. 11 (a)
FIG. 11 (b)

MAT FOR PRESSURE MEASUREMENT AND A BODY INFORMATION ACQUISITION DEVICE

BACKGROUND OF THE INVENTION

1. Field of the Invention

This invention relates to a mat for pressure measurement and a body information acquisition device used thereof.

2. Description of the Related Art

Conventionally, an air mat comprising the sleep cycle sensing device illustrated in Japanese Patent No. 2000-215 is disclosed as a mat for pressure measurement. The air mat comprises an air tube and the inside of the air tube is filled with air in a similar manner to the air mat. A sleep cycle sensing device detects the air pressure and the change amounts in the air tube by the respectively separate sensors, distinguishes whether or not a subject is on an air mat based on the detected air pressure, and measures a subject's body motion based on the change amount of air pressure. Then, a subject's sleep state is estimated based on the measurement result of the body motion.

In the above-mentioned sleep cycle sensing device, since it was not taken into consideration about the type of body motion such as whether a subject's body motion was rolling over or others, the distribution of pressure applied to an air mat could not be measured, even if the change or strength of pressure applied to an air mat could be measured. For this reason, when even the distribution of pressure applied to an air mat by using the above-mentioned air mat was measured, a plurality of detection units in the air mat and the sensor for measuring the pressure applied to the air mat for every detection units were required to be provided.

SUMMARY OF THE INVENTION

The object of the present invention is to provide a mat for pressure measurement and a body information acquisition device used thereof to solve the above-mentioned problems.

In order to accomplish the object, the present invention provides a mat for pressure measurement comprising: a plurality of medium accommodation objects which inside is filled with a pressure transmission medium; and a connecting pipeline provided in the respective medium accommodation objects which lead the pressure inputted into the medium accommodation objects to a pressure detection unit of the pressure transmission medium and which has a different pressure loss coefficient reciprocally.

Also, in the present invention each connecting pipeline has a different size of internal diameter reciprocally.

Also, in the present invention the connecting pipeline with a small internal diameter has a long pipeline length compared to the connecting pipeline with a large internal diameter.

Also, in the present invention the connecting pipeline with a small internal diameter has a converging part with a small open aperture ratio or a large number of converging parts compared to the connecting pipeline with a large internal diameter.

Also, in the present invention the medium accommodation objects with a large pressure loss coefficient of the connecting pipeline which lead the inputted pressure to the pressure detection unit is formed a thick wall compared to the medium accommodation objects with a small pressure loss coefficient of the connecting pipeline which lead the inputted pressure to the pressure detection unit.

Also, in the present invention the respective medium accommodation objects comprises pipelines and the respective accommodation objects having a large pressure loss coefficient of the connecting pipeline which lead the inputted pressure to the pressure detection unit is provided a small internal diameter compared to the medium accommodation objects having a small pressure loss coefficient of the connecting pipeline which lead the inputted pressure to the pressure detection unit.

Also, the present invention provides a body information acquisition device which acquires a subject's body information by using the mat for pressure measurement comprising: a detection means to detect the pressure change in the pressure detection unit; a measurement means to measure the distribution and the strength of the pressure on the mat for pressure measurement based on the pressure change detected by the detection means; and a body position calculation means to calculate the position or the motion of the subject's body on the mat for pressure measurement based on the measurement result by the measurement means.

According to a mat for pressure measurement by the present invention, it becomes possible to measure the distribution of inputted pressure in the similar manner to the strength of applied pressure by a simple configuration of providing one detection means in one pressure detection unit. Also, according to the sleep measuring device in the present invention, it becomes possible to measure the type of a subject's body motion by using a simple configuration of providing one detection means of the pressure applied to the mat for pressure measurement.

BRIEF DESCRIPTION OF THE DRAWINGS

FIG. 1 is an outline drawing showing an outline of a sleep measuring device which is applied the present invention.

FIG. 2(a) is a top view showing an outline of a mat for pressure measurement shown in FIG. 1 and FIG. 2(b) is an A-A line sectional view of FIG. 2(a).

FIG. 3 is a sectional view showing an outline of structures of a sensor unit in a control box as shown in FIG. 1.

FIG. 4 is a block diagram showing an outline of hardware constitutions of a sleep measuring device as shown in FIG. 1.

FIG. 9(a) is a top view showing the first modified example of a mat for pressure measurement and FIG. 9(b) is a B-B line sectional view of FIG. 9(a).

FIG. 10(a) is a top view showing the second modified example of a mat for pressure measurement, and FIG. 10(b) is a C-C line sectional view of FIG. 10(a).

FIG. 11(a) is a top view showing the third modified example of a mat for pressure measurement and FIG. 11(b) is a D-D line sectional view of FIG. 11(a).

DETAILED DESCRIPTION OF THE INVENTION

Figure 5:
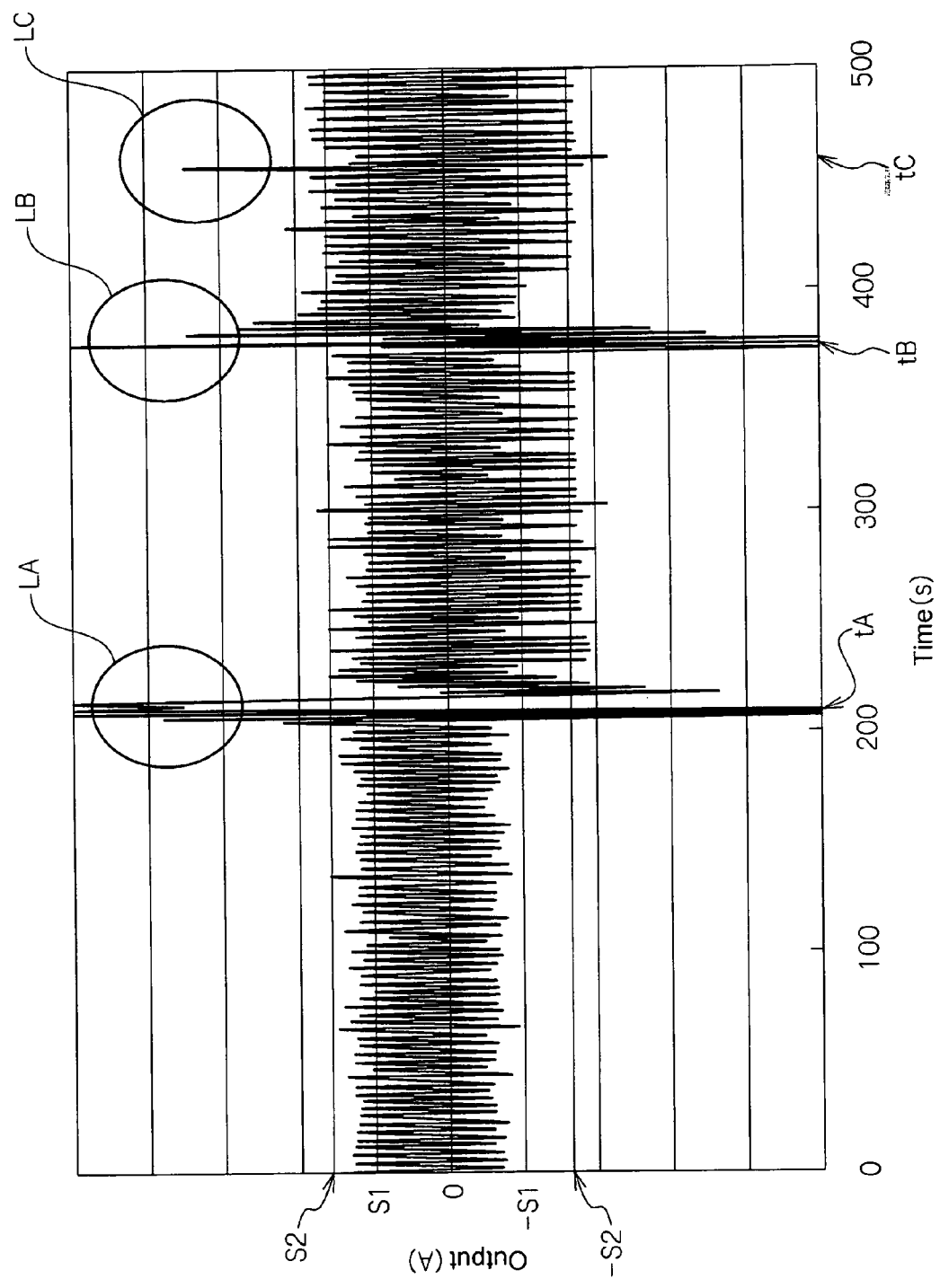
FIG. 5 is a drawing showing a display example of body data to be produced by a calculation control unit in a display unit as shown in FIG. 4.

The preferred embodiments of the invention will be explained with reference to the figures.

FIG. 1 is an outline drawing showing an outline of a sleep measuring device 1 which is applied the present invention.

The sleep measuring device 1 is a device which detects motion originated in body phenomena such as a pulse, breathing, and body motion of subject who laid on a mat for pressure measurement 2 and produces the body data during sleep, and calculates various indices about sleep based on the body data. The sleep measuring device 1 comprises a mat for pressure measurement 2, a control box 4 connected with the mat for pressure measurement 2 by a tube 25, and an external terminal device 5 electrically connected with the control box 4 by a cable line 6. In the present embodiment, the case that a bedding 7 is set up on the mat for pressure measurement 2 and the body data of a subject laid on the bedding 7 are collected by the sleep measuring device 1 is explained.

FIG. 2 is a drawing showing an outline of the mat for pressure measurement 2: FIG. 2(a) is a top view and FIG. 2(b) is an A-A line sectional view of FIG. 2(a). The mat for pressure measurement 2 is formed by pressure bonding with the two sheets made of synthetic resins such as polyvinyl chloride (PVC), polyethylene, or the like. The first pipeline 21 and the second pipeline 22 are formed inside of the mat for pressure measurement 2. The mat for pressure measurement 2 comprises the tube 25 to link to communicate with the first pipeline 21 and the second pipeline 22. The end face 25a of the tube 25 is connected to the left back part of the mat for pressure measurement 2. The tube 25 comprising the mat for pressure measurement 2, and the first pipeline 21 and the second pipeline 22 are filled with for example water as a pressure transmission medium. In the cross direction center of the mat for pressure measurement 2, the flat part 24 formed by pressure bonding with the above mentioned two sheets from the edge part in the front side to nearly the edge part in the back side of the mat for pressure measurement 2.

The first pipeline 21 is extended toward the right direction of the mat for pressure measurement 2 from the left back part of the mat for pressure measurement 2 to nearly the flat part 24 by going back and forth between the front side and the back side of the mat for pressure measurement 2. The first connecting pipeline 21a is provided in the end of the left back part of the mat for pressure measurement 2 in the first pipeline 21. Also the first pipeline 21 installed between the fat part 24 and the first connecting pipeline 21a constitutes the first medium accommodation object 21b. The pressure inputted into the first medium accommodation object 21b is transmitted to the direction showed as the arrow in the first connecting pipeline 21a. The internal diameter K2 of the first connecting pipeline 21a is smaller than the internal diameter K1 of the pipeline which is constituted the first medium accommodation object 21b.

The second pipeline 22 is provided with second medium accommodation object 22b extended to the edge on the right side of the mat for pressure measurement 2 by going back and forth between the front side and the back side of the mat for pressure measurement 2 in second connecting pipeline 22a installed in the left side of the mat for pressure measurement 2 and the right side of the mat for pressure measurement 2. The second connecting pipeline 22a is provided the pipeline 22a5 extended on the edge of the mat for pressure measurement 2 located on the left side of the first medium accommodation object 21b from the left back part of the mat for pressure measurement 2 and the pipeline 22a4 extended to the close position of the flat part 24 on the edge of the mat for pressure measurement 2 located on the front side of the first medium accommodation object 21b from the pipeline 22a5. Also, the second connecting pipeline 22a comprises the pipeline 22a3 extended toward the edge of the back side of the mat for pressure measurement 2 between the first medium accommodation object 21b and the flat parts from the pipeline 22a4, the pipeline 22a2 extended along the edge of the mat for pressure measurement 2 located from pipeline 22a3 to the back side of the flat part 24, and the pipeline 22a1 extended alone the right side edge of the flat part 24 from the pipeline 22a2 to the edge of the front side of the mat for pressure measurement 2. The pressure inputted into the second medium accommodation object 22b is transmitted in the order of the pipeline 22a1, the pipeline 22a2, the pipeline 22a3, the pipeline 22a4, and the pipeline 22a5 in the second connecting pipeline 22a showed as the arrow.

The internal diameter K3 of the second medium accommodation object 22b is almost equivalent length to the internal diameter K1 of the first medium accommodation object 21b. The internal diameter K4 of the second connecting pipeline 22a is smaller than the internal diameter K3 of the pipeline constituted the second medium accommodation object 22b. Also, the first connecting pipeline 21a and the second connecting pipeline 22a have a respectively different pressure loss coefficient. Here, the pressure loss coefficient is defined as a pressure loss value per unit length of pipeline. In the embodiment, since the internal diameter K4 of the second connecting pipeline 22a is smaller than the internal diameter K2 of the first connecting pipeline 21a and the pipeline length of the second connecting pipeline 22a is longer than that of the first connecting pipeline 21a, the pressure loss coefficient of the second connecting pipeline 22a has a greater value than that of the first connecting pipeline 21a.

FIG. 3 is a sectional view showing an outline of structures of a sensor unit 4a in a control box 4. The sensor unit 4a comprises an air chamber 41 and a water chamber 43 which are separated by a pressure receiving membrane 42. The pressure receiving membrane 42 is made by elastic bodies such as rubber. A connection port 44 to the tube 25 is formed in the end of the water chamber 43. A tip 25b of the tube 25 connected with the sensor unit 4a is a pressure detection unit in the mat for pressure measurement 2. A sensor attachment port 45 which is attached a microphone sensor 40 is provided on the end of the air chamber 41. In the sensor unit 4a, the water chamber 43 is filled with water in the similar manner to the first pipeline 21 and the second pipeline 22 by connecting to the tube 25 via the connection port 44. Also, the sensor unit 4a is in a state where a microphone receiving unit 45a of the microphone sensor 40 is exposed in the air chamber 41, by attaching the microphone sensor 40 via the sensor attachment port 45. The sensor unit 4a which has such configuration changes the water pressure change in the water chamber 43 into the air pressure change by the pressure receiving membrane 42, and then captures the air pressure change by the microphone sensor 40 and obtains an output signal.

FIG. 4 is a block diagram showing an outline of hardware constitutions of a sleep measuring device 1. As shown in FIG. 4, the microphone sensor 40 in the control box 4 as mentioned above is electrically connected with the external terminal device 5 via the cable line 6. The external terminal device 5 comprises a calculation control unit (CPU) 51 which performs various kinds of calculation and control, an input unit 52 which consists of a plurality of keys, a display unit 53 which performs various kinds of displays, a transmission and reception unit 54 which performs data communications with the external apparatus including the microphone sensor 40, a clock unit 55 which performs management of time, and a memory unit 56 which memorizes various data used for processing on the calculation control unit 51. The calculation control unit 51 comprises a CPU, a ROM to memorize the control program, and a RAM to use the control program for the calculation or the like.

According to the control of the control program on the calculation control unit 51, the transmission and reception section 54 takes sampling an analog signal inputted from the microphone sensor 40 with the predetermined time interval clocked by a clock unit 55, and changes the analog signal into the digital signal. The calculation control unit 51 memorizes the digital signal inputted from the transmission and reception unit 54 and the lapsed time for sampling as body data on the memory unit 56. Various indices are calculated with the body data memorized on memory unit 56. The display unit 53 displays the indices and body data which are calculated on the calculation control unit 51 based on the control of the calculation control unit 51.

When the signal level inputted from the transmission and reception unit 54 becomes greater than a predetermined value, the calculation control unit 51 detects that the body motion is generated at the time. Also, the calculation control unit 51 takes only a frequency component lower than the general human respiration frequency (about 0.29 Hz) from body data with a low pass filter, and produces respiratory data. Also, after the calculation control unit 51 takes only the predetermined frequency component including the general human pulse frequency (about 0.88 Hz) from body data with a band pass filter and performs full-wave rectification with a full-wave rectification circuit, and produces pulse data. The production can be performed by using the method described in Japanese published patent application no. 2006-280686, which is previously applied by the same applicants as the present application.

As mentioned above, the mat for pressure measurement 2 has a configuration which the pressure loss generated from inputted on the right side providing the second medium accommodation object 22b by being detected on the microphone sensor 40 is greater than that generated from inputted on the left side providing the first medium accommodation object 21b by being detected on the microphone sensor 40. Therefore, even when the pressure applied on the right side and the left side of the mat for pressure measurement 2 is equal, the pressure detection value in the microphone sensor 40 applied on the left side tends to be higher than that applied on the right side. Therefore, when a subject is on left side of the mat for pressure measurement 2, the inputted signal level based on the subject's respiration and pulse tends to be higher than when a subject is on the right side of that.

Therefore, in the embodiment, when the signal level obtained after detecting that the body motion has occurred in the calculation control unit 51 is above the predetermined value compared to that obtained before detecting, a subject is detected to be moved from the right side of the mat for pressure measurement 2 with the second medium accommodation object 21b to the left side of the mat for pressure measurement 2 with the first medium accommodation object 22b. On the other hand, when the signal level is below the predetermined value compared to that obtained before detecting, a subject is detected to be moved from the left side of the mat for pressure measurement 2 with the first medium accommodation object 21b to the right side of the mat for pressure measurement 2 with the second medium accommodation object 22b.

FIG. 5 is a drawing showing a display example of body data to be produced by a calculation control unit 51 in a display unit 53. Body data is shown in the graph which takes the data of lapsed tine (s) along the horizontal axis and the data of the signal output (signal level) (A) along the vertical axis in the example described in FIG. 5. In the body data, although the signal level is maintaining almost constant amplitude S1 (A) from time 0 (s) to about 200 (s), the signal level LA (A) of remarkably high amplitude is obtained at the time tA (s) which passes around 200 (s). Then, although the signal level is decreased, the greater amplitude S2 (A) than the amplitude S1 (A) is maintained. Then, although the signal level LB (A) and LC (A) of remarkable high amplitude is obtained at the time tB(s) which passes around 380 (s) and tC(s) which passes around 460 (s) respectively, the signal level after attenuation is maintained the amplitude S2(A). Therefore, although a subject is detected rolling over from the right side to the left side of the mat for pressure measurement 2 at the time tA (s) by the calculation control unit 51, a subject is detected the other body motions which is not rolling over at the time tB (s) and tC(s).

Figure 6:
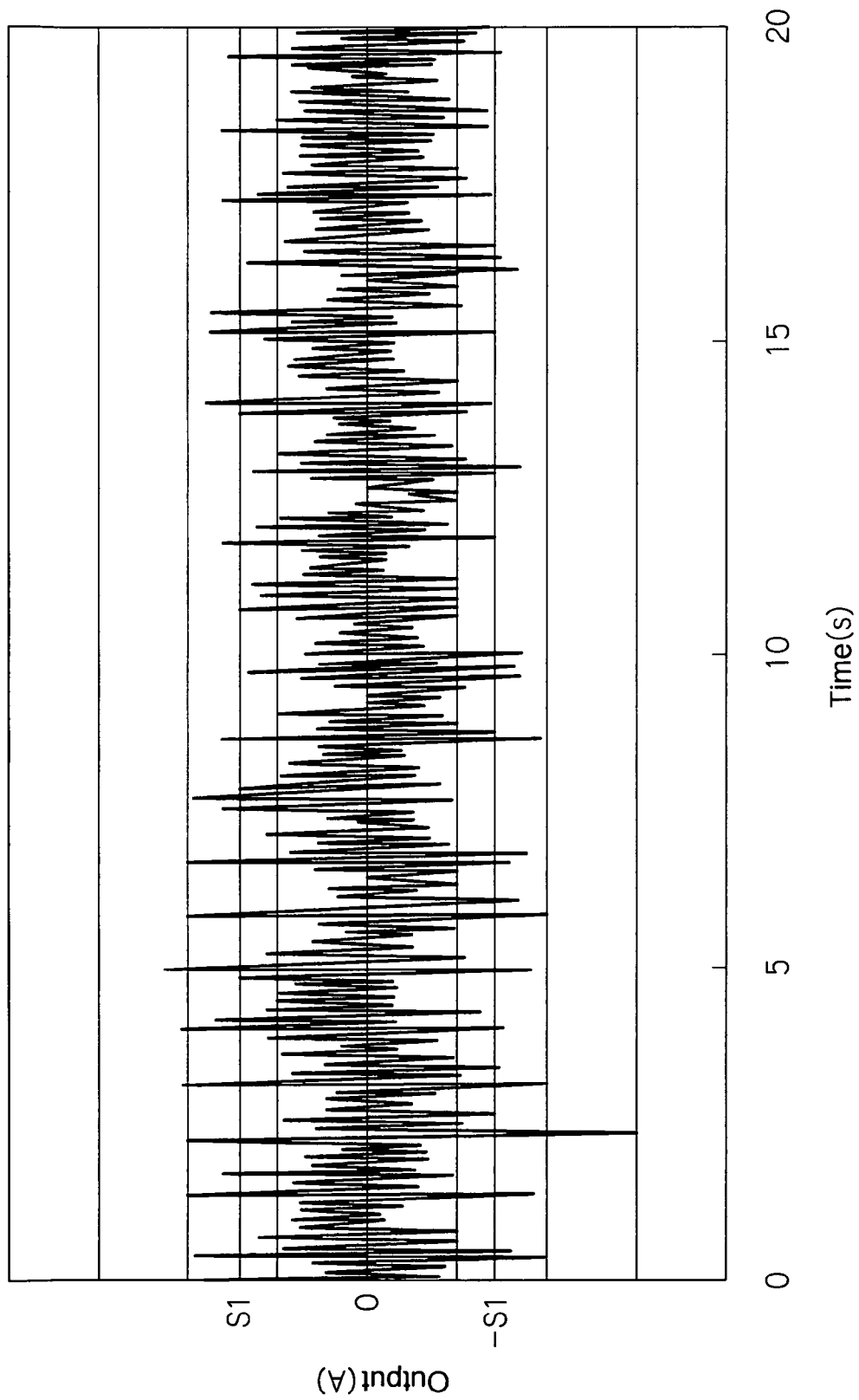
FIG. 6 is a drawing showing a display example of the time from about 0 (s) to 20 (s) of the body data as shown in FIG. 5.
Figure 7:
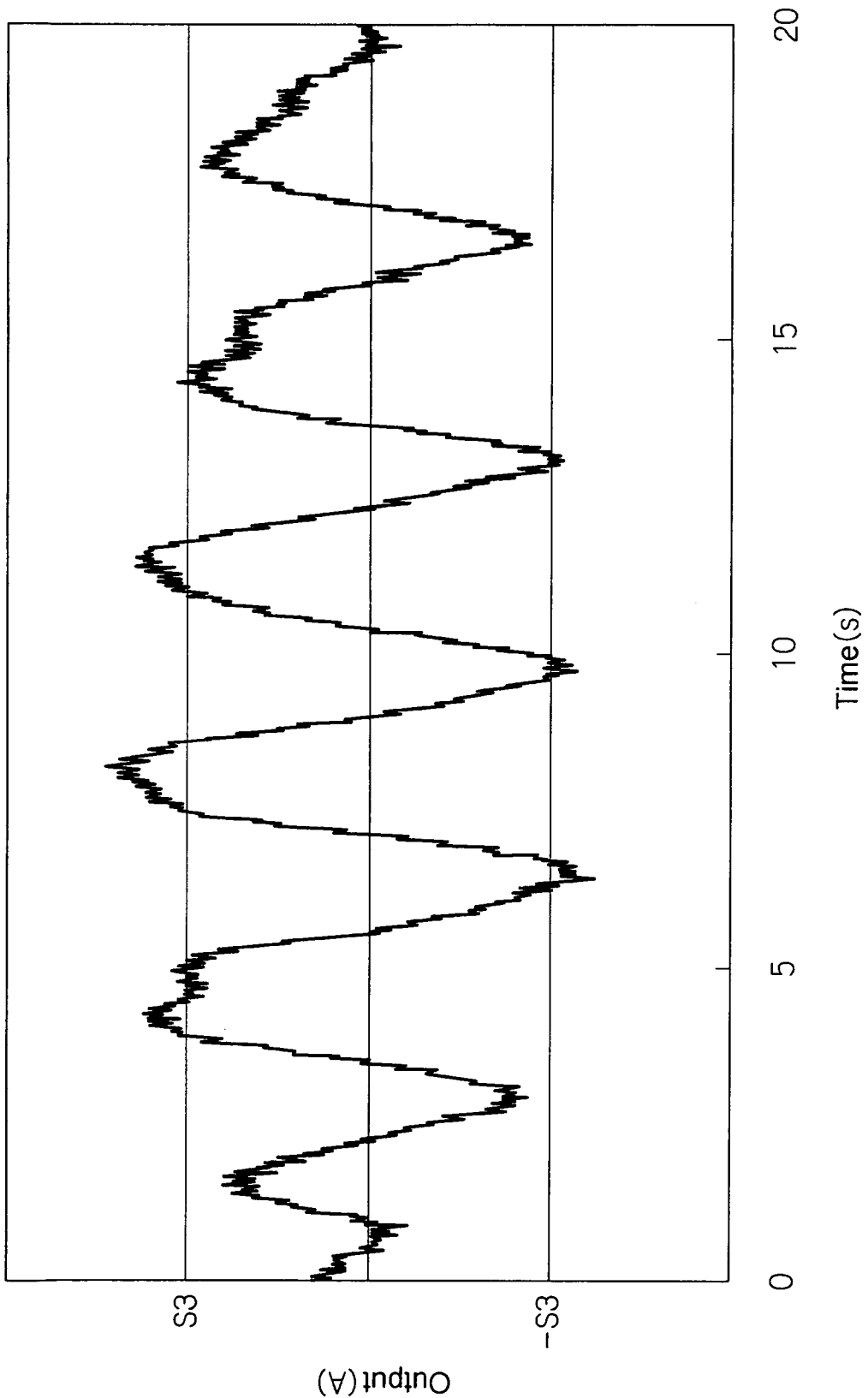
FIG. 7 is a drawing showing a display example of a respiratory data to be produced by an operation control unit based on a body data as shown in FIG. 6.
Figure 8:
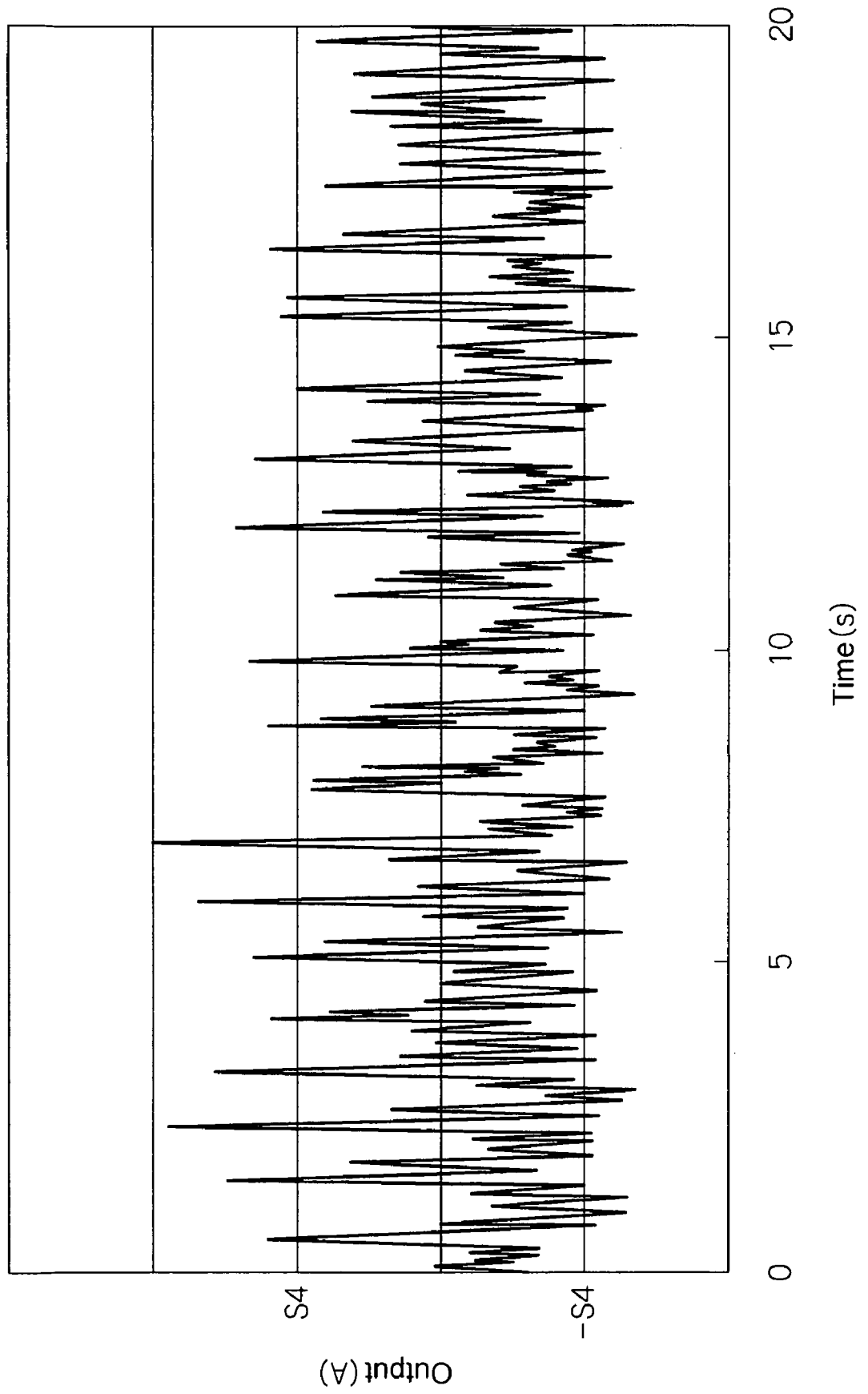
FIG. 8 is a drawing showing a display example of a pulse data to be produced by an operation control unit based on the body data as shown in FIG. 6.

FIG. 6 is an enlarged drawing showing data at time about 0 (s) to 20 (s) of the body data shown in FIG. 5. FIG. 7 is a drawing showing the display example of the respiratory data which the calculation control unit 51 produced based on the body data on the display unit 53 shown in FIG. 6. FIG. 8 is a drawing showing the display example of the pulse data which the calculation control unit 51 produced based on the body data on the display unit 53 shown in FIG. 6. Each data is shown in the graph which takes the data of lapsed time (s) along the horizontal axis and the data of the signal level (A) along the vertical axis in the example shown in each figure.

In the respiratory data shown in FIG. 7, the waveform of the frequency about 0.29 Hz and the amplitude about S3 (A) is observed. It becomes possible to estimate the respiration cycle of about 3.4 second/cycle or the like from the data. In the pulse data shown in FIG. 8, the waveform of the frequency about 0.88 Hz and the amplitude about S4 (A) is observed. It becomes possible to estimate the pulse cycle of about 1.14 second/cycle or the like from the data. Based on these fundamental data, the calculation control unit 51 calculates various data about a subject's sleep state. For example, by calculating the frequency (distribution) of respiration and pulse from these data obtained through a night and then by checking each sleep stage (non-REM and REM), by calculating the variation pattern of respiration and pulse from daily measured value and then by checking the attenuation rate and each sleep stage from the respiration rate and pulse rate under resting conditions, or the like, the appearance ratio of a subject's detailed sleep stage is calculated.

According to the sleep measuring device 1 in the embodiment, since the pressure loss coefficient differs between the first connecting pipeline 21a and the second connecting pipeline 22a, the pressure wastage rate transmitted at the tip 25b of the tube 25 which is a pressure detection unit after passing through each connecting pipelines 21a and 22a also differs respectively. Therefore, even if the same pressure is applied to the mat for pressure measurement 2 from the outside, the pressure detected on the tip 25b of the tube 25 is different values depending on any of the medium accommodation object 21b or 22b is inputted. Therefore, when the pressure as the target for detection such as the regularly inputted pressure or the like based on a laid subject's respiration and pulse on the mat for pressure measurement 2, either the medium accommodation object 21b on the left side of the mat for pressure measurement 2 or the medium accommodation object 22b on the right side is inputted can be estimated based on the detected pressure. As a result, the unit where the pressure is applied on the mat for pressure measurement 2, that is, the distribution of pressure can be measured with the applied pressure by providing one detection means in one pressure detection unit. Therefore, it becomes possible to measure the type of subject's body motion such as rolling over or the like on the mat for pressure measurement 2 by providing one detection means in one pressure detection unit.

As long as the pressure loss coefficients of each connecting pipeline connected to a plurality of medium accommodation objects differ each other, any configuration of the mat for pressure measurement 2 can be considered, for example, the configuration shown in each drawing of FIG. 9-11 can also be considered. FIG. 9 is a drawing showing the mat for pressure measurement 2a in the first modified example of the mat for pressure measurement 2, and (a) is a top view and (b) is a B-B line sectional view of FIG. 9 (a). The mat for pressure measurement 2a is formed so that it may be provided the first pipeline 210, the second pipeline 220, and the tube 250 by pressure bonding with the two sheets in the same manner as the mat for pressure measurement 2. The first pipeline 210 in the same manner as the first pipeline 21 provided on the mat for pressure measurement 2 extends to the cross direction center of the mat for pressure measurement 2a having the flat part 240 corresponding to the flat part 24, and provides the first connecting pipeline 210a corresponding to the first connecting pipeline 21a and the first medium accommodation object 210b corresponding to the medium accommodation object 21b. The pressure inputted into the first medium accommodation object 210b is transmitted in the first connecting pipeline 210a as shown by the arrow.

The second pipeline 220 extends to the right side of the mat for pressure measurement 2 in the same manner as the second pipeline 22 provided on the mat for pressure measurement 2, and provides the second connecting pipeline 220a corresponding to the second connecting pipeline 220a, and the second medium accommodation object 220b corresponding to the second medium accommodation object 22b. The pressure inputted into the second medium accommodation object 220b is transmitted in the second connecting pipeline 220a as shown by the arrow. The internal diameter K20 of the first connecting pipeline 210a and the internal diameter K10 of the first connecting pipeline 210b are set as almost the same values. The internal diameter K40 of the second connecting pipeline 220a is set as a smaller value than the internal diameter K30 of the pipeline which forms the second medium accommodation object 220b. The internal diameter K40 of the second connecting pipeline 220a is set as the value smaller than the internal diameter K20 of the first connecting pipeline 210a. In the example as well as the explanation in the above-mentioned embodiment, since the internal diameter K40 of the second connecting pipeline 220a is set smaller than the internal diameter K20 of first connecting pipeline 210a and the pipeline length of the second connecting pipeline 220a is set longer than the pipeline length of the first connecting pipeline 210a, the pressure loss coefficient value of the second connecting pipeline 220a has a greater value than that of the first connecting pipeline 210a.

Even when the mat for pressure measurement 2a of these compositions is used, the similar operation effect as the above-mentioned embodiment can be obtained. In addition, according to the mat for pressure measurement 2a, since the second medium accommodation object 220b connected to the second connecting pipeline 220a is smaller than the first medium accommodation object 210b connected to the first connecting pipeline 210a, the difference of the pressure loss rate transmitted at the tip 250b of the tube 250 which is a pressure detection unit can be further enlarged. Therefore, the measurement accuracy can be increased in the unit applied the pressure in the mat for pressure measurement 2 based on the difference in the detected pressure.

FIG. 10 is a drawing showing the mat for pressure measurement 2b of the second modified example of the mat for pressure measurement 2, (a) is a top view and (b) is a C-C line sectional view of FIG. 10 (a). The mat for pressure measurement 2b has the composition provided with the first pipeline 211, the second pipeline 221, and the tube 251 in the same manner as the mat for pressure measurement 2. The pressure inputted into the first medium accommodation object 211b is transmitted in the first connecting pipeline 211a as shown the arrow. The pressure inputted into the second medium accommodation object 221b is transmitted in the second connecting pipeline 221a in the order of the pipeline 221a1, the pipeline 221a2, the pipeline 221a3, the pipeline 221a4, and the pipeline 221a5 as shown in the arrow. In the example as well as the explanation in the above-mentioned embodiment, since the internal diameter K41 of the second connecting pipeline 221a is set smaller than the internal diameter K21 of the first connecting pipeline 211a and the pipeline length of the second connecting pipeline 221a is set longer than the pipeline length of the first connecting pipeline 211a, the pressure loss coefficient value of the second connecting pipeline 221a has higher than that of the first connecting pipeline 211a. In the mat for pressure measurement 2b, the wall thickness is different between the pipeline on the left side provided with the first medium accommodation object 211b and on the right side provided with the second medium accommodation object 221b. That is, the mat for pressure measurement 2 is formed by pressure bonding with the two sheets on the left side and it is configured by the total four sheets which is formed by pressure bonding with the pasted two sheets on the right side.

Even when the mat for pressure measurement 2b of these compositions is used, the similar operation effect as the above-mentioned embodiment can be obtained. In addition, according to the mat for pressure measurement 2b, since the second medium accommodation object 221b connected to the second connecting pipeline 221a with a greater pressure loss coefficient is formed with a thicker wall, the difference of the pressure loss rate transmitted to the pressure detection unit can be further enlarged. Therefore, the measurement accuracy can be increased in the unit applied the pressure in the mat for pressure measurement 2b based on the difference in the detected pressure.

FIG. 11 is a drawing showing the mat for pressure measurement 2c in the third modified example of the mat for pressure measurement 2, (a) is a top view and (b) is a D-D line sectional view of FIG. 11 (a). The mat for pressure measurement 2c is provided with the first pipeline 212, the second pipeline 222, and also the third pipeline 232. The first pipeline 212, the second pipeline 222, and the third pipeline 232 extend to the right side of the mat for pressure measurement 2c by going back and forth between the front side and the back side of the mat for pressure measurement 2c on the left, the center, and the right side of the mat for pressure measurement 2c which is divided into three parts in the cross direction, respectively. The pressure inputted into the first medium accommodation object 212b is transmitted in the first connecting pipeline 212a as shown the arrow. The pressure inputted into 2nd medium accommodation object 222b is transmitted in the second connecting pipeline 222a in the order of the pipeline 222a1, the pipeline 222a2, the pipeline 222a3, the pipeline 222a4, and the pipeline 222a5 as shown the arrow. The pressure inputted into the third medium accommodation object 232b is transmitted in the second connecting pipeline 232a in the order of the pipeline 232a1 and the pipeline 232a2 as shown the arrow. In the example, since the internal diameter K62 of the third connecting pipeline 232a and the internal diameter K42 of the second connecting pipeline 222a are set smaller than the internal diameter K22 of the first connecting pipeline 212a and the pipeline length is set longer in the order of the third connecting pipeline 232a, the second connecting pipeline 222a, and the first connecting pipeline 212a, the pressure loss coefficient value is higher in the order of the third connecting pipeline 232a, the second connecting pipeline 222a, and the first connecting pipeline 212a.

Even when the mat for pressure measurement 2c of these compositions is used, the similar operation effect as the above-mentioned embodiment can be obtained. In addition, according to the mat for pressure measurement 2c, since the pressure inputted into any region which is divided into the left side, the central part, and the right side can be measured, the measurement accuracy can be increased in the part applied the pressure in the mat for pressure measurement 2c.

Although the case that water is used as a pressure transmission medium to be filled in the mat for pressure measurement 2 is explained, any pressure transmission medium can be used, for example, the air can also be used to be filled. Also, in the explanation of above-mentioned embodiment, although the case that the mat for pressure measurement 2 is put on the bottom of the bedding 7 which a subject actually lies on is explained, a subject can directly lie on the mat for pressure measurement 2 and can be measured the respiration, pulse, and body motion.

Also, in the explanation of above-mentioned embodiment, the mat for pressure measurement 2 is divided into the right side and the left side from the cross direction center, and the case of measurement that a subject is located either on the left side or on the right side of the mat for pressure measurement 2 is explained. However, a medium accommodation object is provided on each region by dividing the mat for pressure measurement 2 into several pieces from the front side to the back side and further dividing it into several pieces from the right side to the left side and each medium accommodation object can be connected to the connecting pipes which differ the pressure loss coefficient. Also, the pressure loss rate inputted into each medium accommodation object 21b and 22b can be differently provided by changing the material which forms each medium accommodation object 21b and 22b, and each connecting pipeline 21a and 21b. For example, by using polyethylene on the left side of the mat for pressure measurement 2 and polyvinyl chloride on the right side, or by using rigid polyvinyl chloride on the left side and soft polyvinyl chloride on the right side, the pressure loss rate of each medium accommodation object 21b and 22b and each connecting pipeline 21a and 21b can be changed.

Also, in the explanation of above-mentioned embodiment, although the case that the pressure loss coefficient is changed by setting the internal diameter and length of each connecting pipeline 21a and 22a as a different value is explained, the pressure loss coefficient can be different by forming a converging part such as an orifice or the like in each connecting pipeline 21a and 22a. For example, the pressure loss coefficient can also be different by changing the open aperture ratio of the converging part provided in each connecting pipeline 21a and 22a and the number of the converging parts. Also, the pressure loss coefficient can also be different by providing the different number or the different open aperture ratio of the converging part in each connecting pipeline 21a and 22a which differs the internal diameter and length. For example, one converging part can be provided in the connecting-pipeline 21a and more than two multiple converging parts can be provided in the connecting pipeline 22a. Also, the pressure loss coefficient can also be different by changing the number or the shape of the flection parts provided in each connecting, pipeline.

Also, in the explanation of above-mentioned embodiment, although the case that the position of the subject on the mat for pressure measurement 2 is measured based on the pressure applied to the mat for pressure measurement 2 by mainly a subject's respiration and pulse is explained, when the pressure intensity applied to the mat for pressure measurement 2 can be estimated to some extent, the position of the subject on the mat for pressure measurement 2 can also be measured based on the pressure change applied to the mat for pressure measurement 2 by the other factor.

Also, any type of sensor can be provided in the sensor unit and the pressure sensor by using a condenser microphone or a piezoresistance effect, the pressure sensor by using the piezo-electric effect, or the like can be used. Also, the external terminal device 5 is not limited to a personal computer but can be used the other proper measurement device. Also, the connecting pipeline which leads each medium accommodation object 21b and 22b to the pressure detection unit does not need to be a pipeline formed integrally in the medium accommodation object 21b and 22b, and any configuration can be used. Also, the medium accommodation object does not need to be provided a pipeline but can be used any shape, for example, the medium accommodation object which is the bag-like object can also be used. Also, in the explanation of above-mentioned embodiment, the case that the tip 25b of the tube 25 is the pressure detection unit in the mat for pressure measurement 2 is explained, any position of pressure detection unit is used. For example, the mat for pressure measurement 2 can be configured without the tube 25 and connecting a sensor as a pressure detection unit on the left back part of the mat for pressure measurement 2.

In the explanation of above-mentioned embodiment, the case that the present invention is applied to the sleep measuring device 1 which acquires the information on rolling over as a type of body motion. However, the body information acquisition device of the present invention can also acquire the information on the other type of body motion such as spasm, convulsion accompanying epilepsy seizure, or the like based on the pressure intensity and distribution applied from a subject's body on the mat for pressure measurement 2.

In the explanation of the above-mentioned embodiment, since the differences of the loss rate of the pressure inputted from the outside on the left side and the right side of the mat for pressure measurement 2 is relatively not so large compared with that of the level of the input signal based on respiration, pulse, or the like, the case that body data is produced by using directly the input signal from the sensor unit 4a is explained. However, the configuration which can amplify the signal level of the input signal or the body data from the sensor unit 4a can be used and the configuration which detects the position of the subject on the mat for pressure measurement 2 based on acquiring the body data at a certain amplification stage after detecting the body motion can be used. For example, in the case that the body motion generates when the body data can be acquired in a certain amplification stage and then the body data cannot be acquired in the amplification stage within predetermined time, the amplification stage is increased and decreased, and ii the amplification stage is increased and the body data can be obtained, the subject is detected to move on the right side from the left side of the mat for pressure measurement 2. On the other hand, if the amplification stage is decreased and the body data can be obtained, the subject is detected to move on the left side from the right side of the mat for pressure measurement 2. According to the configuration, in the case that the difference of the loss rate of the pressure inputted from the outside on the left side and the right side of the mat for pressure measurement 2 is prominently large or small compared with the level of the input signal based on respiration, pulse, or the like, the subject is on which side, on the left or the right, can be detected.

Also, in the explanation of above-mentioned embodiment, the case that the motion of the subject on the mat for pressure measurement 2 based on the body data mixed with the respiratory data and the pulse data is explained. However, in the case that the sufficient difference for the loss rate of the pressure inputted on the right side and the left side of the mat for pressure measurement 2 can be provided, the configuration which detects the motion of the subject on the mat for pressure measurement 2 based on the change of the signal level of the respiratory data, the pulse data, or the like generated by the body data can be used.

Also, in the explanation of above-mentioned embodiment, based on whether or not the signal level obtained after detecting the body motion is larger than a predetermined value compared to the signal level obtained before the detection, that is, based on the change amount of the signal level, the case that the position and the motion of the subject is detected on the mat for pressure measurement 2 is explained. However, in the case that the signal level which is obtained based on the respiration or the pulse can be estimated by a certain measurement condition, for examples the subject always lies on the mat for pressure measurement 2, the configuration that the position and the motion of the subject is detected on the mat for pressure measurement 2 can be used.

In the explanation of above-mentioned embodiment, the case that the mat for pressure measurement in the present invention is used for obtaining the subject's body data in sleep measuring device 1 as a body information acquisition device is explained. However, the mat for pressure measurement in the present invention is not limited to these devices but can be used in combination with the other device. For example, the mat for pressure measurement which applied the present invention is covered on the indoor floor or the like and the position and posture of human body or the like inside the room is detected based on the pressure inputted into the mat for pressure measurement, and the operation state of the home electronics including the air conditioner can also be controlled based on the detection result.

What is claimed is:

1. A body information acquisition device which acquires a subject's body information comprising:
    a mat for pressure measurement comprising: a plurality of medium accommodation objects which inside is filled with a pressure transmission medium; and a connecting pipeline provided in the respective medium accommodation objects which lead the pressure inputted into the medium accommodation objects to one detection means to detect the pressure change in one pressure detection unit for the pressure transmission medium and each connecting pipeline has a different size of internal diameter and a different pressure loss coefficient reciprocally;
    a detection means to detect the pressure change in the pressure detection unit;
    a measurement means to measure the distribution and the strength of the pressure on the mat for pressure measurement based on the pressure change detected by the detection means; and
    a body position calculation means to calculate the position or the motion of the subject's body on the mat for pressure measurement based on the measurement result by the measurement means.

2. The body information acquisition device according to claim 1, wherein the connecting pipeline in the mat for pressure measurement with a small internal diameter has a long pipeline length compared to the connecting pipeline with a large internal diameter.

3. The body information acquisition device to claim 1, wherein the connecting pipeline in the mat for pressure measurement with a small internal diameter has a converging part with a small open aperture ratio or a large number of converging parts compared to the connecting pipeline with a large internal diameter.

4. The body information acquisition device according to claim 1, wherein the medium accommodation objects in the mat for pressure measurement with a large pressure loss coefficient of the connecting pipeline which leads the inputted pressure to the pressure detection unit is formed with a thick wall compared to the medium accommodation objects with a small pressure loss coefficient of the connecting pipeline which leads the inputted pressure to the pressure detection unit.

5. The body information acquisition device according to claim 1, wherein the respective medium accommodation objects in the mat for pressure measurement comprise pipelines and the respective medium accommodation objects having a large pressure loss coefficient of the connecting pipeline which lead the inputted pressure to the pressure detection unit is provided with a small internal diameter compared to the medium accommodation objects having a small pressure loss coefficient of the connecting pipeline which leads the inputted pressure to the pressure detection unit.

* * * * *